(12) United States Patent
Ray

(10) Patent No.: US 6,852,095 B1
(45) Date of Patent: Feb. 8, 2005

(54) INTERBODY DEVICE AND METHOD FOR TREATMENT OF OSTEOPOROTIC VERTEBRAL COLLAPSE

(76) Inventor: Charles D. Ray, 125 Alexander Walker, Kings Mill on James, Williamsburg, VA (US) 23185

(*) Notice: Subject to any disclaimer, the term of this patent is extended or adjusted under 35 U.S.C. 154(b) by 0 days.

(21) Appl. No.: 09/807,318
(22) PCT Filed: Jul. 9, 1998
(86) PCT No.: PCT/US98/14146
§ 371 (c)(1),
(2), (4) Date: Mar. 14, 2002
(87) PCT Pub. No.: WO99/02214
PCT Pub. Date: Jan. 21, 1999

Related U.S. Application Data
(60) Provisional application No. 60/052,849, filed on Jul. 9, 1997.

(51) Int. Cl.[7] .............................................. A61M 31/00
(52) U.S. Cl. .................... 604/93.01; 606/93; 604/96.01
(58) Field of Search .............................. 606/92, 93, 94, 606/60, 61, 62, 86, 91, 191, 192, 193, 194; 623/7; 604/96.01

(56) References Cited
U.S. PATENT DOCUMENTS 6,241,734 B1 * 6/2001 Scribner et al. .............. 606/93
6,248,110 B1 * 6/2001 Reiley et al. ................. 606/93

* cited by examiner

Primary Examiner—Manuel Mendez

(57) ABSTRACT

The present invention is an apparatus for repairing a collapsed space within vertical bodies. The apparatus includes an introducer (20) including an elongate member having proximal, distal ends, and defining a longitudinal bore. The elongate member includes a threaded portion adjacent the distal end, being configured for insertion into vertebral bodies to facilitate mounting of the elongate member to the vertebral bodies, and a catheter at least partially positioned within the longitudinal bore of the elongate members of the introducer (20). The catheter includes a catheter body member having proximal, and distal ends, an inflation lumen extending along at least a portion of the catheter body, and an expandable membrane adjacent the distal end of the catheter body member in fluid communication with the inflation lumen. The expandable membrane is extendable beyond the distal end of the introducer (20), and positioned between the vertebral bodies. The expandable membrane is expandable in response to inflation fluids conveyed by the inflation lumen to exert a force on the vertebral bodies to achieve a desired spacing therewith. A method of reforming a collapsed vertebra utilizing the apparatus is also disclosed.

15 Claims, 3 Drawing Sheets

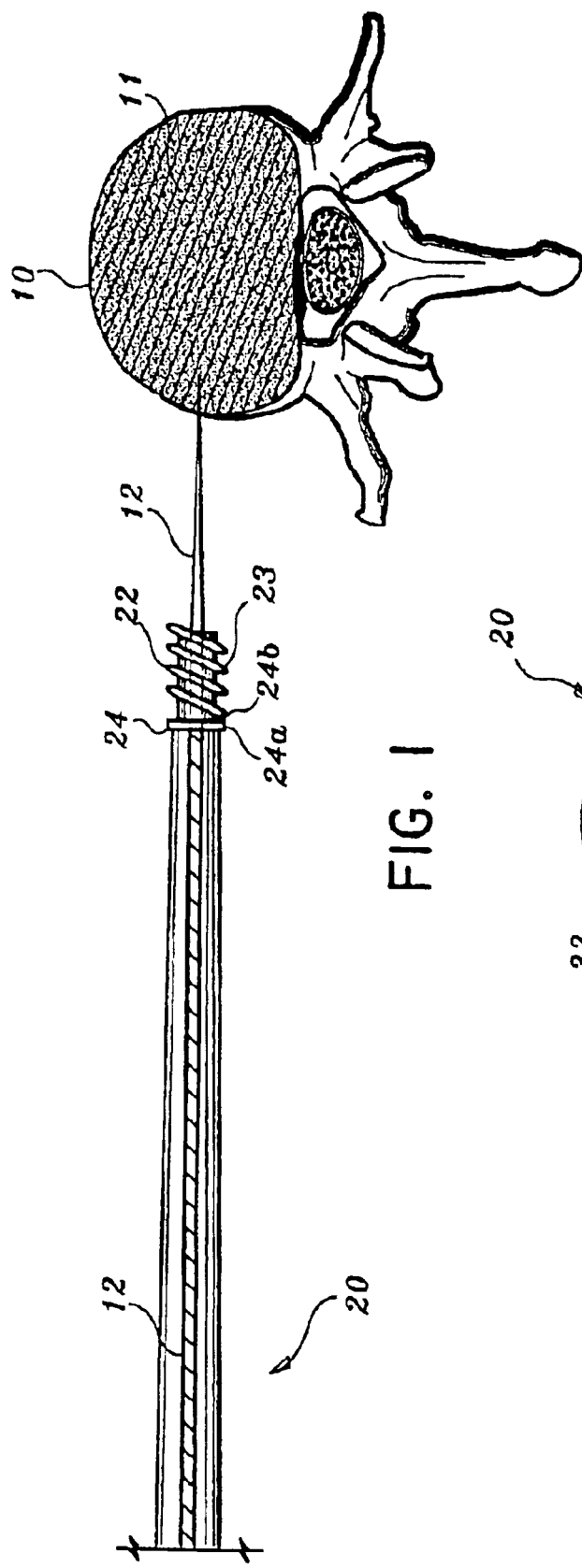
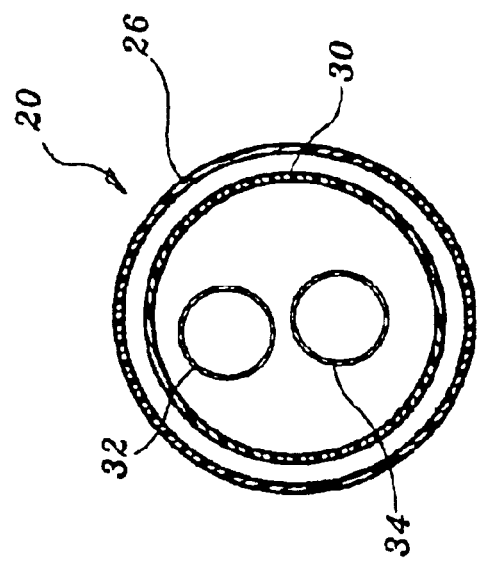
FIG. 1
FIG. 3

INTERBODY DEVICE AND METHOD FOR TREATMENT OF OSTEOPOROTIC VERTEBRAL COLLAPSE

CROSS-REFERENCE TO RELATED APPLICATIONS

This patent application claims the benefit of U.S. Provisional Application No. 60/052,849 filed Jul. 9, 1997, the contents of which are incorporated herein by reference.

BACKGROUND

1. Technical Field

The present disclosure relates to an apparatus and method for treating a structural collapse of the human vertebrae, and more particularly, to an intervertebral device for treating collapsed vertebrae due to osteoporotic weakening.

2. Background of Related Art

Osteopenia is a bone condition resulting in a reduction in the normal content of the mineral calcium within a bone. The lack of calcium and associated collagen matrix, which binds the calcium into the bone structure, results in a weakening of the overall bone strength Osteoporosis, the pathological weakening of bone by severe demineralization, is brought about by advanced osteopenia and gives rise to significantly higher incidences of bone fractures. Osteopenia or osteoporosis in the spine can result in fracture collapse of one or more vertebrae or bone segments thereby shortening and deforming the spine. In some cases, these deformities inhibit a person's ability to function normally and may also affect a person's ability to breathe normally due to the collapse of the vertebral segments. These fractures or deformities are found most commonly among post-menopausal women, since it is known that the body's circulating level of the female hormone estrogen has a direct effect on osteopenia. Thus, when a woman's ovaries are either removed or stop manufacturing the estrogen hormone, osteoporosis is more likely to occur which could result in multiple bone fractures throughout the body.

Osteoporotic fractures are a common health problem and generally occur principally at the wrists, hip joints, ribs and collar bones. However, collapses involving the vertebrae, while the most common, are the least understood of the various fractures. Upon collapse of a spinal vertebra, the collapsing vertebra is transformed into the shape of a wedge having the narrow portion directed towards an anterior direction (front), thus causing the spine to exhibit the classic forward bending and the formation of a posterior hump. The collapse is usually opposite and away from the posterior compartment or spinal canal housing the spinal cord. A lesser occurring collapse of the posterior compartment of a spinal vertebra may result in a patient suffering from myelopathy due to cord compression. This total collapse of the vertebra with nearly complete loss of the vertebral body mass in all dimensions is quite rare except in some cases of metastatic cancer where the collapse may compress the spinal cord resulting in paraplegia or death.

Once the osteoporotic bone of the spine has become soft enough to permit a collapse under a relatively normal load, other bones or additional levels of the spine often fracture as well. This cascade of fractures creates a deformed, shortened spinal column. Secondary problems may then arise, such as interference with normal breathing, gait disturbance and a social stigma against the person's appearance. Collapse of a vertebral body occurs when there is a sudden increase in loading beyond that which the bone can tolerate, sometimes as the result of a normal event like sneezing or picking up a light object. The membrane surrounding the vertebral bone, the periosteum, is richly innervated with pain fibers which when disturbed by vertebral collapse administer pain signals, as well as, incite the formation of new bone growth. The vertebral collapse causes a loss of the contained vertebral bone marrow and an associated loss of vertebral body height. Due to a difference in construction and metabolism, the outer hard cortical enclosure of the vertebral bone does not suffer as much loss of mineral or strength as the softer interior cancerous bone.

The most important risk factors for bone fractures are an individual's: (1) age, (2) genetic factors, (3) environmental factors, (4) hormone levels, (5) presence of chronic diseases, and (6) the physical or radiologic characteristics of the bone. Although the true incidence of vertebral fracture is unknown, the evidence is clear that it increases exponentially with age in much the same way as for hip fractures. Between the ages of 60 and 90 years the incidence of vertebral fracture rises approximately 20-fold in women compared to a 50-fold increase in the risk of hip fracture. The problem of vertebral collapse is not limited to women alone, studies have shown that vertebral osteoporosis is seen in over 20% of men and women and is correlated with low dietary calcium intake and low serum vitamin D levels. Additional significant risk factors included cigarette smoking, low physical activity and long-term immobilization. The lowest levels of bone density were seen in women who suffered vertebral collapse fractures, most commonly in those having early menopause. It has also been shown that when the deformity or collapse of the vertebral bone segment is 4 cm or greater in vertebral height the likelihood of back pain is 2.5 times greater than when the collapse is of a lesser height. This likelihood is independent of how many vertebral levels are involved in fractures or whether or not the deformity involves anterior wedging, end plate failure or vertebral body crush. It is clear that vertebral collapse fractures are a significant clinical and economic problem.

The best treatment for osteoporosis is prevention particularly since the loss of bone strength that accompanies bone loss is not known to be reversible. Identification of those at risk by measurement of risk factors may help target prevention efforts. Many of the factors that are known to increase fracture risk in susceptible patients can be treated. Appropriate care or correction of risk factors include cigarette smoking, low circulating estrogen (usually associated with menopause), low physical activity and long-term immobilization, low dietary calcium intake and low serum vitamin D levels. Other treatable risk factors include: peptic ulcer, tuberculosis and illnesses or conditions that may cause dizziness, weakness and falling. These factors are particularly important in the elderly. It is clear that appropriate diet, exercise and supportive treatments are helpful in nearly all cases. However, a very large number of cases are not preventable since they are strongly influenced by genetic, medical or environmental circumstances. In such cases, certain new drugs including oral alendronate, an aminobisphosphonate or bisphosphonated etidronate taken daily, can progressively increase the bone mass (strength) in the body, including the spine and hip areas. Such treatments can reduce the incidence of vertebral fractures, the progression of vertebral fracture deformities and height loss in post-menopausal osteoporotic women. Unfortunately, these drugs have no beneficial effect to reverse the collapse after it has occurred. In fact, regardless of the predisposing factors, once the collapse has occurred, pain control and immobilization are essentially the only current treatments available. There exists no present method that can acutely reverse the collapse, lead to reconstitution of the vertebra and relieve the severe associated pain. The current mode of treatments include bed rest, the wearing of a rigid brace, sedatives, muscle relaxers, physical therapy modalities and other palliative measures. These treatments exhibit some value in pain reduction but generally the fractured or collapsed vertebra must be stabilized or fused for the severe pain to effectively subside.

More recently, spinal supporting injections of fast setting substances into the collapsed vertebrae have been used to fixate the vertebral collapse in order to stop the pain and suffering. Such injection substances include tricalcium phosphate, calcium carbonate, calcium hydroxyapatite, all of which act essentially like plaster of Paris. These injection materials will stop the progression of the vertebral collapse and subsequently be slowly converted into bone and thereby restore the strength of the collapsed segment. Also used as injection materials are polymerics, such as, fast setting polymethylmethacrylate mixed with powdered barium making the injected materials visible on X-ray images. However, none of these fast-setting materials and associated methods of use restore vertebrae height. In order to re-inflate or re-form the collapsed vertebra and restore the vertical height, the materials would have to be injected within the vertebrae under considerable pressure (up to 8 or 10 atmospheres, 116 to 145 psi 510 to 638 Newtons) so as to overcome the collapsing force, muscle pull and tissue recoil subjected upon the vertebra. At such high injection pressure, the injected material may leak through the fractured or collapsed portions of the vertebra and enter the adjacent major vessels, possibly causing an immediate and potentially lethal blockage. Further, these materials and other self-curing thermoplastics are highly viscous and cannot be injected through a reasonably sized hypodermic tube, cannula, catheter or introducer. The use of these materials also generate significant heat which may damage the sensitive bone cells leading to bone atrophy and delayed integration. In addition, the above-mentioned polymerics do not form or integrate into new bone and as such may create a new problem where the bone and the plastic material have a zone of non-union or pseudoarthrosis.

The embodiments of the present disclosure are described here to overcome the above limitations and achieve the goals of re-inflating or re-forming partially collapsed vertebrae, to restore the vertebral height, stabilize the fracture, integrate the injected material into bone and alleviate the severe pain associated with osteoporotic collapse. In addition, the techniques described herein may also be used in certain cases of complete or partial vertebral body collapse from erosion of the bone by a metastatic cancer or the like.

SUMMARY

The present disclosure is directed to an intervertebral apparatus and method for treating collapsed vertebrae due to osteoporotic weakening and collapse of vertebrae. The interbody device and method for treatment of osteoporotic vertebral collapse is specifically designed to re-establish or reform the lost vertebrae height attributable to debilitating orthopedic diseases such as osteoporosis and osteopenia Accordingly, an apparatus for repairing a collapsed space within vertebral bodies is disclosed. The apparatus includes an introducer including an elongate member having proximal and distal ends and defining a longitudinal bore. The introducer further includes a projection along an external length thereof, the projection facilitating the rotation of the threaded portion into the vertebral bodies. The elongate member includes a threaded portion adjacent the distal end and being configured for insertion into vertebral bodies to facilitate mounting of the elongate member to the vertebral bodies and a catheter at least partially positionable within the longitudinal bore of the elongate member of the introducer. The threaded portion of the elongate member further includes a collar, the collar having an elastic seal adapted to form a seal along an external portion of the vertebral bodies.

The catheter includes a catheter body member having proximal and distal ends, an inflation lumen extending along at least a portion of the catheter body and an expandable membrane adjacent the distal end of the catheter body member in fluid communication with the inflation lumen. The expandable membrane is extendible beyond the distal end of the introducer and positionable between the vertebral bodies. The expandable membrane is expandable in response to inflation fluids conveyed by the inflation lumen to exert a force on the vertebral bodies to achieve a desired spacing therewithin. The apparatus includes a source of inflation fluid in communication with the inflation lumen to expand the expandable membrane. The source of inflation fluid includes an injected bone growth inducing material.

Preferably, the apparatus also includes a treating agent delivery lumen extending along at least a portion of the catheter body and in fluid communication with an interior of the vertebral bodies An injection device is coupled to at least one of the inflation lumen and treating agent delivery lumen for providing the inflation fluids to the expandable membrane and to the treating agent delivery lumen for providing bone growth inducing materials within the interior of the vertebral bodies. The injection device is preferably a high injection pressure syringe.

Preferably, the expandable membrane is releasably attached to the catheter body member. An uncoupling sleeve is mounted about the elongate member of the introducer, wherein the uncoupling sleeve is movable to separate the expandable membrane from the catheter body member.

A method for reforming a collapsed vertebra is also disclosed. The method includes the steps of mounting an introducer to vertebral body portions to access a collapsed area therewithin, the introducer defining a longitudinal bore. Inserting a catheter within the longitudinal bore of the introducer, wherein the catheter includes a catheter body having an expandable membrane mounted adjacent a distal end thereof. Positioning the expandable membrane within the collapsed area of the vertebral body portions and expanding the expandable membrane whereby the expandable membrane exerts a force on the vertebral body portions to increase a dimension of the collapsed area to achieve a desired spacing therewithin. The expanding step includes inflating the expandable member with inflation fluids. The catheter body includes a delivery lumen terminating in an opening in the catheter body member and wherein the step of injecting includes introducing the treating agent into the delivery lumen to be conveyed thereby and dispensed through the opening.

Preferably, the method further includes the step of injecting a treating agent into the collapsed area of the vertebral body portions to facilitate bone growth within the collapsed area of the vertebral bodies.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages may best be understood by reference to the following description, taken in connection with the accompanying drawings, in which:

FIG. 1 is a schematic view of the interbody device according to the present disclosure illustrating a guide needle and associated introducer;

FIG. 3 is a cross-sectional view of the introducer along lines 3—3 of FIG. 2;

DETAILED DESCRIPTION OF PREFERRED EMBODIMENTS

Figure 2:
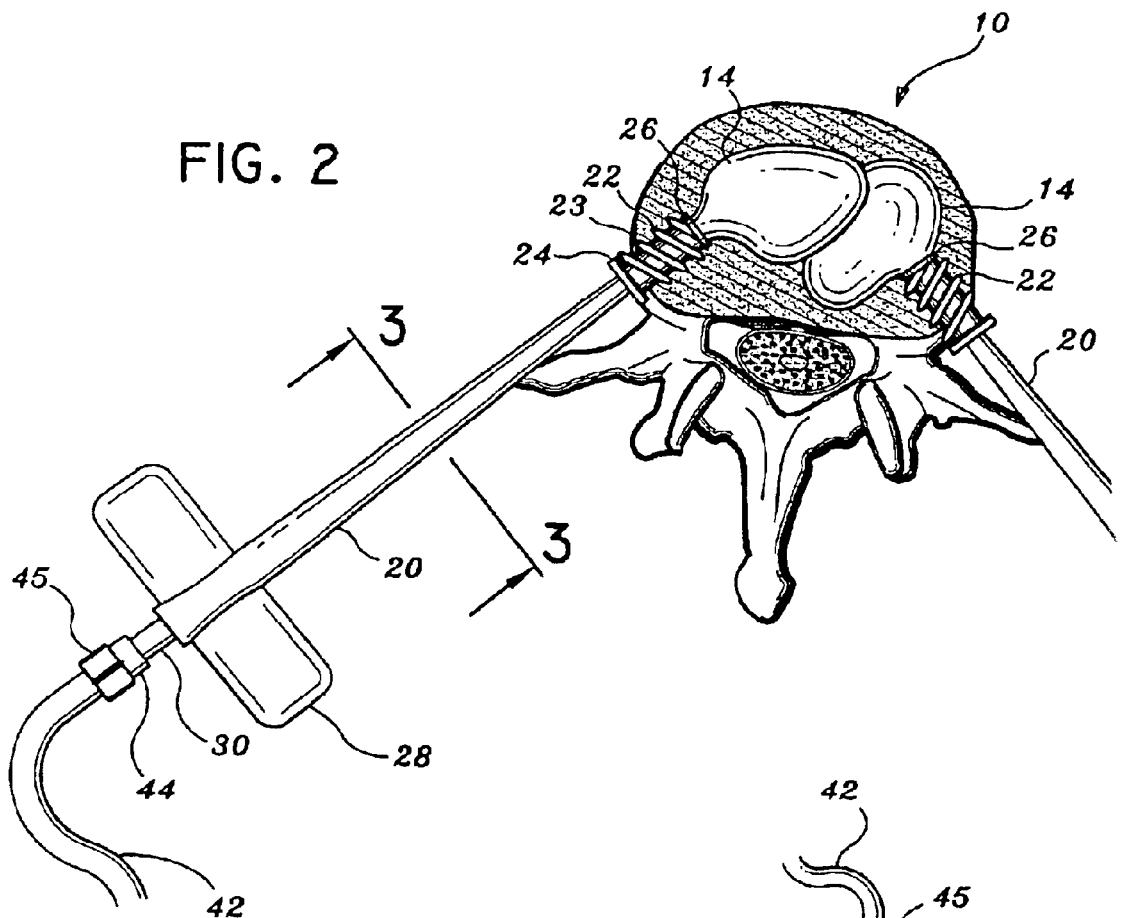
FIG. 2 is a view illustrating a cross-sectional diagrammatic view of a typical vertebra of the spine.

The preferred embodiments of the apparatus and methods disclosed herein are discussed in terms of orthopedic vertebral procedures and instrumentation thereof. It is envisioned, however, that the disclosure is applicable to a wide variety of procedures including, but, not limited to joint repair, non-union fractures, spinal stabilization and the like. In addition, it is believed that the present method and instrumentation finds application in both open and mininally invasive procedures including endoscopic and arthroscopic procedures wherein access to the surgical site is achieved through a cannula or small incision.

In the discussion which follows, the term "proximal", as is traditional, will refer to the portion of the structure which is closer to the operator, while the term "distal" will refer to the portion which is further from the operator.

The following discussion includes a description of the interbody vertebral device followed by a description of the preferred method for treatment of osteoporotic vertebral collapse in accordance with the present disclosure.

Reference will now be made in detail to the preferred embodiments of the disclosure, which are illustrated in the accompanying figures. Turning now to the figures, wherein like components are designated by like reference numerals throughout the various figures, attention is first directed to FIGS. 1–3. In preferred embodiments, one or more interbody devices may be simultaneously used to re-inflate and/or reform a collapsed spinal vertebrae. FIG. 1 is a cross-sectional representation of a collapsed vertebral spinal segment 10 with guide needle 12 engaged within its collapsed interior 11. The percutaneous insertion of each guide needle 12 is preferably performed under the visual aide of a continuous fluoroscopic contrast agent to ensure the proper alignment of guide needles 12 within vertebral interior 11. Endoscopic visual techniques are contemplated as well. Preferably, a first and second guide needle 12 (not shown) is placed from each side of the back or chest into the collapsed vertebra 10 along an insertion path through a narrow access between the costovertebral junctions. Once both guide needles 12 are in a correct position, an introducer 20 with auger tip 22 and sealing member 24 is inserted over each needle 12 and subsequently screwed into the vertebral body 10.

With reference to FIG. 2, each introducer 20 includes butterfly shaped thumbscrew projections 28 for manually twisting the auger-like threaded tip 22 into the outer shell of the vertebral body 10. Each auger threaded tip 22 includes double start threads 23 having a high pitch so as to facilitate the initial biting into and penetration through the tough outer cortex of the vertebra 10. The auger threaded tip 22 facilitates in positioning, fixating or mounting introducer 20 to the vertebral body 10. At the base of the threaded portion 23 of the auger tip 22, there is a sealing member 24 which includes a small collar 24a and an elastic seal 24b adjacent the collar. During insertion of the auger tip 22 within the vertebra 10, the collar 24a acts as a stop against the vertebral body 10 while the elastic seal 24b assists in preventing the escape of marrow and injected materials from leaking out through the bore created by the introducer 20. It is contemplated that the interbody device according to the present disclosure can be manufactured in various sizes appropriate for the safe insertion of the needles 12 and introducers 20 through the lateral structures of vertebral bodies of various dimensions.

Upon proper seating of introducers 20 within vertebra 10, guide needles 12 are removed from the introducers 20 through a proximal end thereof. As is best shown in FIGS. 2 and 3, each catheter 30 includes a first lumen 32 and a second lumen 34 located in each introducer 20. At a distal end of catheter 30 is attached at least one balloon or cuff 14 preferably manufactured of a thin, flexible, high-pressure polymeric material as is known in the art. Once inflated, the balloons 14 are dimensioned to conform to the pre-collapse interior dimensions of the particular vertebra being reformed. The two balloons 14 are positioned bilaterally into the central marrow area of vertebral space 11 of the collapsed vertebra 10. To aide in the visualization of the internal structure of vertebral space 11 and in the proper placement of auger tips 22 and balloons 14, the fluoroscopic contrast agent may be injected through the lumens 32 or 34 into vertebral space 11 and be viewed through X-ray images as is known in the art.

The balloons 14 are preferably manufactured to withstand high pressures (up to 10 atmospheres) and retain a volume of up to 10 ml., although balloons meeting other pressures and volumes are contemplated. In other preferred embodiments, the balloon attachment to catheter 30 and associated lumens 32 and 34 is separable by an uncoupling member or device to permit the balloons 14 to be permanently left within the vertebral space 11. One example of an uncoupling member includes a sleeve 26 (FIG. 3) which is slidably mounted over catheter 30 and movable in a distal direction to slide the balloon 14 off the distal end of the catheter 30. With this arrangement, balloon 14 would be self-sealing, whereby upon removal, the proximal end of the balloon 14 attached to the catheter 30 would close or seal. The uncoupling sleeves 26 are especially beneficial when the balloons 14 are filled with a hardening material, as will be discussed below. In addition, the balloon membranes may be manufactured from a biodegradable material so as to permit time controlled dissolving of the balloons 14 to thereby expose the hardening materials contained therein to the interior of vertebral space 11. Such biodegradable balloon membranes may be manufactured from known materials such as a polylactic acid polymer, a polygalactone biodegradable film, a hydrogel membrane such as polyvinyl acetate or an acrylonitrile. Further, the balloons 14 can be fabricated where only selected segments of the balloon's membrane would slowly dissolve when exposed to body fluids. This feature initially maintains the internal balloon pressure but allows the contained injected material to slowly integrate into the recipient bone of vertebra 10.

Figure 4:
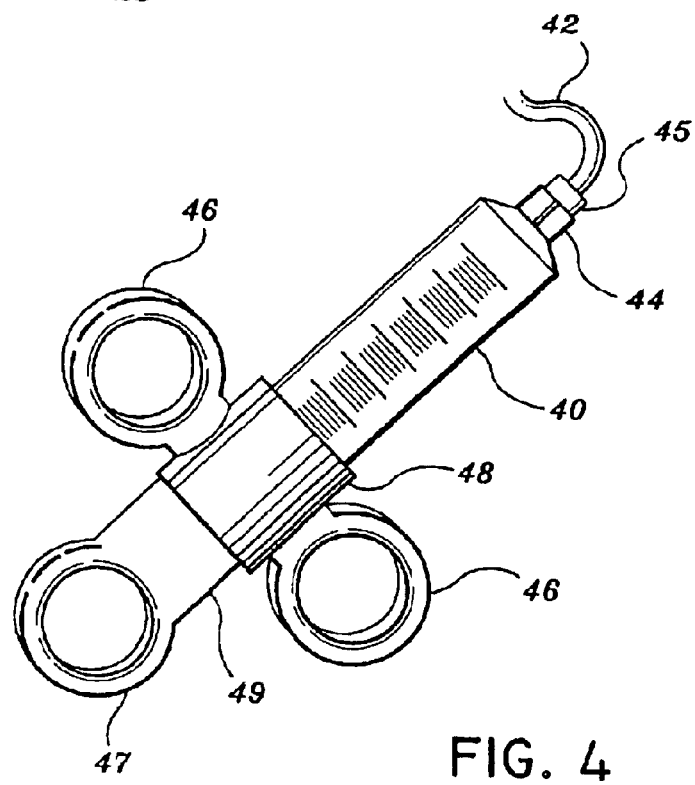
FIG. 4 is an oblique isometric view illustrating a hand-held, three-ring pressure syringe according to the present disclosure.

With particular reference to FIG. 4, a single hand operated syringe 40 is shown although, as will be discussed below, as many as four syringes 40 may be used to inject materials through lumens 32 and 34 of catheter 30. As such, the syringes 40 of the present disclosure are preferably used to hydraulically inflate balloons 14 and to inject medicants within vertebral space 11, although other similar injection/inflation devices such as pumps, squeezable membranes or the like may be used. Each lumen 32 and 34 engages a separate syringe 40 which acts to inflate balloon 14 and inject medicants within vertebral space 11, respectively. Syringes 40 are preferably three-ring pressure syringes having finger rings 46 on a collar 48 and a thumb ring 47 on plunger portion 49. As noted above, the syringes 40 may be filled with a combination of injectable materials and/or solutions including sterile saline solution, fluoroscopic contrast agent, bone growth inducing materials, hardening materials and the like. The injectable materials may be a slurry of calcium complex known to integrate into bone with a supporting polymeric filler to improve strength until the fracture has healed or fused. Additionally, a bone growth factor, such as bone morphogenic protein may be added to the injectate to facilitate the rapid growth of firm bone within vertebra 10. As will be discussed below, each balloon 14 is inflated separately with a particular solution or combination thereof dependent upon the anatomical conditions of the collapsed vertebrae 10. The syringes 40 are connected to catheter 30 and lumens 32 and 34 via high-pressure flexible polymeric tubing 42. The tubing 42 is attached to each lumen 32 and 34 and respective syringes 40 with Luer connections 44. Valves structures 45 are placed in-line along Luer connections 44, tubing 42 or syringes 40 to maintain the inflation pressure in each balloon 14 once inflated. Syringes 40 are capable of manually providing high amounts of injection pressure (8 or 10 atmospheres) to balloons 14. Through these high injection pressures, the syringe solution inflates balloons 14, as well as, cause each balloon 14 to internally dissect or collapse the cancerous matrix of the vertebral marrow within vertebral space 11 thereby creating a cavity within the vertebral body 10.

Figure 5:
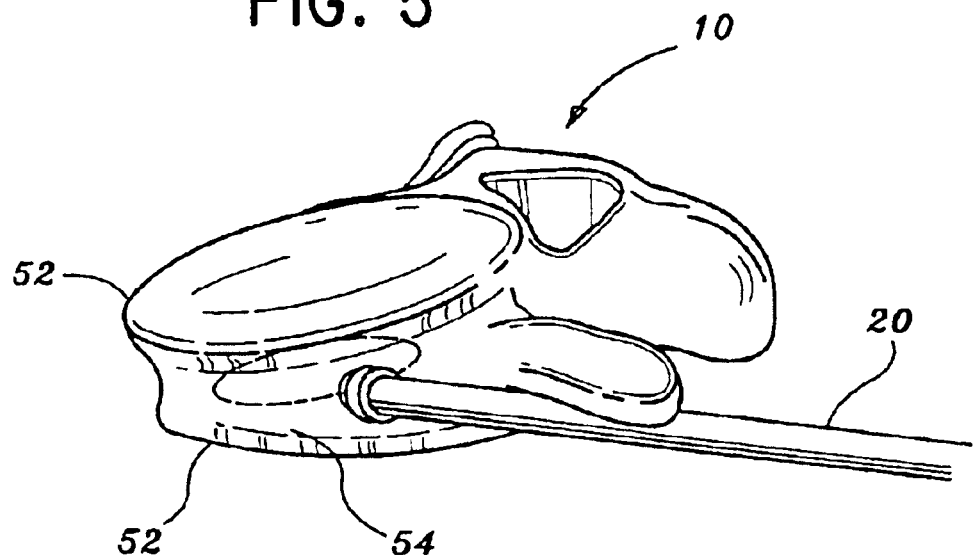
FIG. 5 is a lateral isometric view illustrating a partially collapsed vertebra prior to reforming.
Figure 5A:
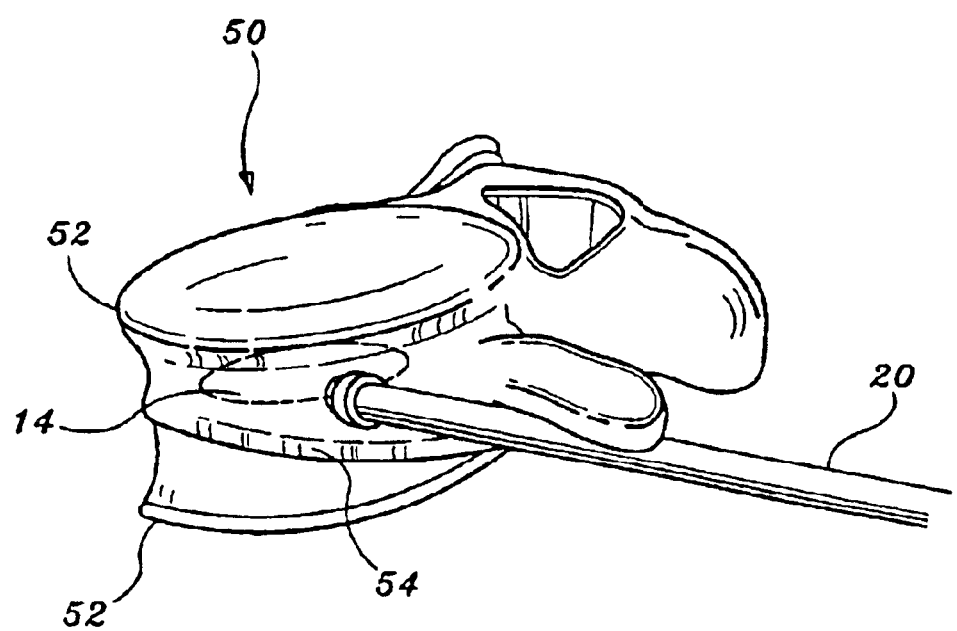
FIG. 5A is lateral isomeric view illustrating a reformed vertebra utilizing the interbody device according to the present disclosure.

As best seen in FIGS. 5 and 5A, the inflation of balloons 14 create a cavity within vertebral body 10 and cause the hardened end plates 52 of vertebra 10 to separate and expand to a point 50 restoring the normal pre-collapse vertebral height of vertebra 10. In cases where the side cortical wall 54 of vertebra 10 is imperfect or broken, the dimensions of the balloons 14 are such that, upon inflation, the balloons 14 are maintained within the confines of the vertebral space 11.

The method of treating osteoporotic vertebral collapse according to the present disclosure will now be described. The method utilizes a controlled and monitored technique which is simple to perform and provides relative safe effective treatment for the patient. Preferably, the method is performed percutaneously as opposed to open surgery. The procedure is performed under aseptic conditions in the operating room or in a standard cardiac catheterization room in the X-ray department The patient is partly anesthetized and sedated using appropriate intravenous medications. The patient is suspended in a chest and underarm supporting harness to overcome forces such as gravity and muscle spasms in the thoracic and lumbar spinal segments. These forces participate in the collapsing force imparted on the vertebrae and must be overcome to facilitate the re-expansion of the collapsed vertebral bodies. Utilizing an image-amplifying fluoroscope, X-ray, CT scanner or the like, the points of entry and trajectory to the target vertebrae are noted and marked on the overlying skin. Attention to the patient's anatomical detail is necessary to avoid potential serious damage to structures normally found adjacent to the vertebrae, such as, segmental blood vessels and spinal nerves, as well as, avoiding penetration of the lungs and other tissue.

Upon proper alignment of the patient and through guided images (X-ray or the like) guiding needles 12 are placed well into the center of the affected vertebral body 10 from a posterolateral approach. A small amount of X-ray opaque contrast dye such as OMNIPAQUE (TM) or HYPAQUE (TM) is injected through each needle 12 to ensure that the needles 12 are properly situated within the vertebrae. A small amount of local anesthetic may also be injected within vertebra 10 to reduce the pain and to determine that the particular collapsed vertebra is causing the pain experienced by the patient. Subsequent to proper insertion of needles 12 within the collapsed vertebra 10, introducers 20 are passed over the needles at the insertion points of the vertebra 10. With the aid of the auger-like threaded tips 22 of introducers 20, each introducer 20 is screwed into the cortical or lateral wall 54 of the collapsed vertebral body 10 using thumbscrew wings 28 positioned proximally on the introducers 20. The guide needles 12 are then removed. Catheter 30 includes at least one balloon 14 distally situated and coupled to a first 32 or second 34 lumen which is introduced within each catheter 30. One lumen 32 may be used to inflate balloon 14 while a second lumen 34 may be provided for the injection of materials such as contrast agent or bone fixation materials into the surrounding vertebral space 11.

After insertion within the collapsed vertebra 10, both balloons 14 are hydraulically inflated using a solution of sterile saline and fluoroscopic contrast agent. It is contemplated that the other solutions or mixtures previously described herein may also be used to inflate the balloons 14 or be injected within the vertebral space 11. While under close observation via an X-ray monitor, the syringe 40 is compressed creating a pressure, this pressure inflates balloons 14 and correspondingly expands vertebral space 11. As this pressure increases, the expanding balloons 14 create a cavity within the central soft bone area of vertebral space 11. As the balloons 14 are further inflated, the pressure resistant end plates 52 of vertebra 10 are pushed apart from their collapsed form to a point that substantially restores the original vertebral disc height of the collapsed vertebra 10.

Once the balloons 14 are inflated, the tissue is allowed several minutes to accommodate to the pressures and alterations in the restored vertebral bone shape. A first balloon 14 is then deflated leaving a cavity. Into this cavity, rapidly hardening materials such as bone growth inducing materials are injected through lumen 34 of catheter 30 with the use of, e.g., a syringe 40 discussed above. These hardening materials may be a calcium based self-curing material combined with bone morphogenic protein or similar fusion-inducing bone growth factor, as previously described. Alternatively, either or all of the balloons 14 fabricated from an absorbable material may be filled with the rapid hardening, bone growth inducing material and left permanently within the vertebral space 11, as discussed hereinabove. Due to the use of two or more inflated balloons 14 within the vertebral space 11, the deflation of a first balloon 14 does not render a re-collapse of the vertebra 10 because the remaining one or more inflated balloons 14 provide sufficient vertical support to vertebra 10. Therefore, a first balloon 14 is deflated and removed. The second balloon 14 is then deflated and its cavity is likewise injected with bone growth inducing substance or the like. The introducers 20 with auger-like tips 22 are then unscrewed and removed from the body.

The patient will preferably remain in the traction rigging, or wear a rigid supporting brace for a matter of several minutes or hours as the setting process proceeds to completion. A brace might be required for a matter of weeks in some cases. Over time the injected bone-inducing hardened material will be replaced by bone material providing a rigid vertebral segment. The pain and deformity are thus treated rapidly with a desired long-term result.

It will be understood that various modifications may be made to the embodiments disclosed herein. For example, the number and size of balloons 14 inflated within the vertebral space 11 may vary dependent upon the specific ailment, dimensions, and anatomical variants of the diseased vertebrae. Also, the number of lumens 32, 43 within introducer 20 and corresponding materials transported therein may vary to accommodate delivery of solutions, bone growth inducing substances, anesthetic, contrast agent (fluoroscopic solution) and any combination thereof to the vertebral space 11 of vertebra 10. Therefore, the above description should not be construed as limiting, but merely as exemplifications of preferred embodiments. Those skilled in the art will envision other modifications within the scope and spirit of the claims appended hereto.

What is claimed is:

1. An apparatus for repairing a collapsed space within vertebral bodies, which comprises:

an introducer including an elongate member having proximal and distal ends and defining a longitudinal bore, the elongate member having a threaded portion adjacent the distal end and being configured for insertion into vertebral bodies to facilitate mounting of the elongate member to the vertebral bodies; and a catheter at least partially positionable within the longitudinal bore of the elongate member of the introducer, the catheter including a catheter body member having proximal and distal ends, an inflation lumen extending along at least a portion of the catheter body and an expandable membrane releasably attached to the distal end of the catheter body member in fluid communication with the inflation lumen, the expandable membrane extendible beyond the distal end of the introducer and positionable within the vertebral bodies and being expandable in response to inflation fluids conveyed by the inflation lumen to exert a force on the vertebral bodies to achieve a desired spacing therewithin.

2. The apparatus according to claim 1, wherein the catheter further includes a treating agent delivery lumen extending along at least a portion of the catheter body and in fluid communication with an interior of the vertebral bodies.

3. The apparatus according to claim 2, further comprising an injection device coupled to at least one of the inflation lumen and treating agent delivery lumen for providing the inflation fluids to the expandable membrane and to the treating agent delivery lumen for providing bone growth inducing materials within the interior of the vertebral bodies.

4. The apparatus according to claim 3, wherein the injection device is a syringe.

5. The apparatus according to claim 1, wherein the introducer further includes a projection along an external length thereof, the projection facilitating the rotation of the threaded portion into the vertebral bodies.

6. The apparatus according to claim 1, wherein the threaded portion of the elongate member further includes a collar, the collar having an elastic seal adapted to form a seal along an external portion of the vertebral bodies.

7. The apparatus according to claim 1, further including an uncoupling sleeve mounted about the elongate member of the introducer, the uncoupling sleeve movable to separate the expandable membrane from the catheter body member.

8. The apparatus according to claim 1, further including a source of inflation fluid in communication with the inflation lumen to expand the expandable membrane, the source of inflation fluid including an injected bone growth inducing material.

9. The apparatus according to claim 1, wherein at least a portion of the expandable membrane is formed of a biodegradable material.

10. The apparatus according to claim 9, wherein an entirety of the expandable membrane is biodegradable.

11. A method for reforming a collapsed vertebra of a patient, comprising the steps of:

suspending the patient in a chest supporting harness;

mounting an introducer to vertebral body portions to access a collapsed area therewithin, the introducer defining a longitudinal bore;

inserting a catheter within the longitudinal bore of the introducer, the catheter including a catheter body having an expandable membrane mounted adjacent a distal end thereof;

positioning the expandable membrane within the collapsed area of the vertebral body portions; and expanding the expandable membrane whereby the expandable membrane exerts a force on the vertebral body portions to increase a dimension of the collapsed area to achieve a desired spacing therewithin.

12. The method according to claim 11, further including the step of injecting a treating agent into the collapsed area of the vertebral body portions to facilitate bone growth within the collapsed area of the vertebral bodies.

13. The method according to claim 12 wherein the catheter body includes a delivery lumen terminating in an opening in the catheter body member and wherein the step of injecting includes introducing the treating agent into the delivery lumen to be conveyed thereby and dispensed through the opening.

14. The method according to claim 11, wherein the step of expanding includes inflating the expandable member with inflation fluids.

15. The method according to claim 11, further comprising:

dispensing a hardening material into the expandable membrane;

uncoupling the expandable membrane from the catheter body; and removing the catheter body from the patient such that the expandable membrane containing the hardening material remains between the vertebral body portions.

* * * * *